United States Patent
Kim et al.

(10) Patent No.: US 10,645,962 B2
(45) Date of Patent: May 12, 2020

(54) STRAIN ISOLATED FROM TRADITIONAL MEJU, SOYBEAN KOJI PREPARATION METHOD USING SAME, AND SOYBEAN KOJI PREPARED BY THE SAME PREPARATION METHOD

(71) Applicant: CJ Cheiljedang Corporation, Seoul (KR)

(72) Inventors: Hye Jin Kim, Gyeonggi-do (KR); Dong Joo Shin, Gyeonggi-do (KR); Hye Won Shin, Seoul (KR); Eun Seok Jang, Gyeonggi-do (KR); Dae Ik Kang, Gyeonggi-do (KR); Byoung Seok Moon, Gyeonggi-do (KR); Seon Mi Oh, Gyeonggi-do (KR); Sun A Cho, Gyeonggi-do (KR)

(73) Assignee: CJ Cheiljedang Corporation, Jung-Gu (KR)

( * ) Notice: Subject to any disclaimer, the term of this patent is extended or adjusted under 35 U.S.C. 154(b) by 0 days.

(21) Appl. No.: 15/757,097

(22) PCT Filed: Sep. 1, 2016

(86) PCT No.: PCT/KR2016/009804
§ 371 (c)(1),
(2) Date: Mar. 2, 2018

(87) PCT Pub. No.: WO2017/039361
PCT Pub. Date: Mar. 9, 2017

(65) Prior Publication Data
US 2018/0242619 A1   Aug. 30, 2018

(30) Foreign Application Priority Data
Sep. 3, 2015   (KR) .................... 10-2015-0124820

(51) Int. Cl.
*C12N 1/20* (2006.01)
*C12P 1/04* (2006.01)
(Continued)

(52) U.S. Cl.
CPC ............... *A23L 11/09* (2016.08); *A23L 11/00* (2016.08); *A23L 11/20* (2016.08); *A61K 36/48* (2013.01);
(Continued)

(58) Field of Classification Search
None
See application file for complete search history.

(56) References Cited

U.S. PATENT DOCUMENTS 3,914,436 A * 10/1975 Nakadai .................. A23L 27/50
426/46
2010/0120119 A1   5/2010 Sugimoto et al.

FOREIGN PATENT DOCUMENTS

EP          218967 A     9/1986
JP      2008-222701 A    9/2008
(Continued)

OTHER PUBLICATIONS

EP Search Report dated Jan. 31, 2019 in EP 16842327.5, 8 pages.
International Search Report mailed in PCT/KR2016/009804 dated Dec. 8, 2016.

*Primary Examiner* — Blaine Lankford
*Assistant Examiner* — Lauren K Van Buren
(74) *Attorney, Agent, or Firm* — Adsero IP

(57) ABSTRACT

The present disclosure relates to a *Bacillus amyloliquefaciens* CJ14-6 strain isolated from traditional meju, a preparation method for soybean koji using the same, and a soybean koji prepared by the preparation method. The preparation method for soybean koji includes: soaking soybeans in water or adding waster to soybeans and steaming the soaked soybeans; and inoculating a *Bacillus amyloliquefaciens* CJ14-6 strain into the steamed soybeans, fermenting the steamed soybeans, and drying the fermented soybeans to prepare a soybean koji.

4 Claims, 1 Drawing Sheet
Specification includes a Sequence Listing.

(51) Int. Cl.
*A23L 11/00* (2016.01)
*C12R 1/07* (2006.01)
*A23L 11/20* (2016.01)
*A61K 36/48* (2006.01)

(52) U.S. Cl.
CPC .................. *C12N 1/20* (2013.01); *C12P 1/04* (2013.01); *C12R 1/07* (2013.01); *A23V 2002/00* (2013.01); *A23V 2200/3204* (2013.01)

(56) References Cited

FOREIGN PATENT DOCUMENTS

| | | | |
|---|---|---|---|
| JP | 2012-191899 A | | 10/2012 |
| KR | 10-2013-0033026 A | | 4/2013 |
| KR | 2013-0085602 A | | 7/2013 |
| KR | 2014-0047982 A | | 4/2014 |
| KR | 20140047982 | * | 4/2014 |
| KR | 10-2014-0057436 A | | 5/2014 |
| KR | 10-2014-0072338 A | | 6/2014 |
| KR | 2014-0069999 A | | 6/2014 |
| KR | 10-2014-0123847 A | | 10/2014 |
| KR | 10-2015-0089321 A | | 8/2015 |
| RU | 2409659 C2 | | 1/2011 |
| WO | WO 2014-069922 | | 2/2015 |
| WO | WO 2015-122717 A1 | | 8/2015 |

* cited by examiner

SEQUENCE LISTING

<160> NUMBER OF SEQ ID NOS: 1

<210> SEQ ID NO 1
<211> LENGTH: 1418
<212> TYPE: DNA
<213> ORGANISM: Bacillus amyloliquefaciens

<400> SEQUENCE: 1

```
agtcgagcgg acagatggga gcttgctccc tgatgttagc ggcggacggg tgagtaacac      60
gtgggtaacc tgcctgtaag actgggataa ctccgggaaa ccggggctaa taccggatgg     120
ttgtttgaac cgcatggttc agacataaaa ggtggcttcg gctaccactt acagatggac     180
ccgcggcgca ttagctagtt ggtgaggtaa cggctcacca aggcgacgat gcgtagccga     240
cctgagaggg tgatcggcca cactgggact gagacacggc ccagactcct acgggaggca     300
gcagtaggga atcttccgca atggacgaaa gtctgacgga gcaacgccgc gtgagtgatg     360
aaggttttcg gatcgtaaag ctctgttgtt agggaagaac aagtgccgtt caaatagggc     420
ggcaccttga cggtacctaa ccagaaagcc acggctaact acgtgccagc agccgcggta     480
atacgtaggt ggcaagcgtt gtccggaatt attgggcgta aagggctcgc aggcggtttc     540
```

-continued

```
ttaagtctga tgtgaaagcc cccggctcaa ccggggaggg tcattggaaa ctggggaact    600
tgagtgcaga agaggagagt gggagtacca cgtgtagcgg tgacatgcgt agagatgtgg    660
aggaacacca gtggcgaagg cgactctctg gtctgtaact gacgctgagg agcgacagcg    720
tggggagcga acaggattag atacctggt agtccacgcc gtaaacgatg agtgataagt     780 gttaggggggt ttccgcccctt tagtgctgca gctaacgcat taagcactcc gcctggggag  840
tacggtcgca agagtgaaac tcaaaggaat tgacggggggc ccgcacaagc ggtggagcat   900
gtggtttaat tagaagcaac gcgaagaacc ttaccaggtc ttgacatcct ctgacaatcc    960
tagagatagg acgtccccctt cggggggcaga gtgacaggtg gagcatggtt gtcgtcagct 1020
cgtgtcgtga gatgttgggt taagtcccgc aacgagcgca acccttgatt ttagttgcca  1080
gcattcagtt gggcactcta aggtgactgc cggtgacaaa ccggaggaag gtggggatga  1140
cgtcaaatca tcatgcccct tatgacctgg gttacacacg tgttacaatg gacagaacaa  1200
agggcagcga aaccgcgagg ttaagccaat cccacaaatc tgttttcagt tcggatcgca  1260
gtctgcaact cgactgcgtg aagctggaat cgctagtaat cgcggatcag catgccgcgg  1320
tgaatacgtt cccgggcctt gtacacaccg cccgtctctc cacgagagtt tgtaacaccc  1380
gaagtcggtg aggtaacctt ttaggagcca gccgccga                           1418
```

STRAIN ISOLATED FROM TRADITIONAL MEJU, SOYBEAN KOJI PREPARATION METHOD USING SAME, AND SOYBEAN KOJI PREPARED BY THE SAME PREPARATION METHOD

RELATED APPLICATIONS

This application is a National Stage Entry of International Application No. PCT/KR2016/009804 filed on Sep. 1, 2016, and claims the benefit of Korean Application No. 10-2015-0124820, filed on Sep. 3, 2015, which is hereby incorporated by reference in its entirety for all purposes as if fully set forth herein.

The instant application contains a Sequence Listing which has been filed electronically in ASCII format and is hereby incorporated by reference in its entirety. Said ASCII copy, created on Feb. 28, 2018, is named 0117_104_SL.txt and is 2,375 bytes in size.

TECHNICAL FIELD

The present disclosure relates to a novel *Bacillus amyloliquefaciens* CJ14-6 strain isolated from traditional meju and having high protease activity and anti-obesity activity, a preparation method for soybean koji using the novel strain, and a soybean koji prepared by the preparation method.

BACKGROUND ART

Meju is a fermented food that serves as the basis of traditional Korean fermented soybean foods, such as ganjang (soy sauce), gochujang (chili paste), and doenjang (soybean paste). Meju, made from soybeans as a principal ingredient, is also a starter of great importance for the preparation of traditional Korean condiments, that is, ganjang (soy sauce), gochujang (red chili paste), and doenjang (soybean paste).

Meju (fermented soybean) is largely classified into traditional meju, modified meju, or industrial koji (Kokja) depending on the preparation method. The traditional meju is made from, soybeans alone that are shaped, wrapped with rice straws, and then fermented for a defined period of time. The modified meju is prepared from soybeans steamed and fermented with a strain of *Aspergillus* sp. The industrial koji is produced by fermentation of wheat grains or wheat flour with *Aspergillus oryzae*.

Gochujang (red chili paste) is largely classified into traditional (Korean style) gochujang and factory-made (modified) gochujang according to the preparation method. The traditional gochujang is a fermented condiment made from meju powder for gochujang (a mixture of soybean and grains at a given ratio), a starchy ingredient like glutinous rice, yeotgireum (barley malt powder), salt, and chili powder, through fermentation and aging. The factory-made gochujang is an aged diastatic gochujang using a koji with cultured *Aspergillus oryzae*; in place of meju powder for gochujang. In the production of koji, the protein ingredient is soybean; and the starchy ingredient is rice or wheat flour.

As more women enter the workforce outside the home, more people purchase factory-made gochujang. Hence, the production of factory-made gochujang is increasing, and the gochujang export is also on the rise.

As a conventional method to produce factory-made gochujang, KR Patent No. 10-0668056 discloses a soybean meju and its preparation method, where cultured microorganisms are inoculated into soybeans to ferment the soybeans. More specifically, the prior art describes a preparation method for soybean meju and a soybean meju prepared by the method, which method includes a steaming step of steaming and drying soybeans, and a fermentation step of inoculating cultured microorganisms isolated from traditional meju into the soybeans and then fermenting the soybeans for a defined period of time.

Even using the conventional method, there is still a demand for development of a soybean koji for large-quantity production of factory-made gochujang.

PRIOR TECHNICAL DOCUMENTATIONS (Patent Reference 1) KR 10-0668056 B1 (published on Jan. 11, 2007)

DISCLOSURE OF INVENTION

In an attempt to study for the large-quantity production of factory-made gochujang, the inventors of the present disclosure have found out the fact that a *Bacillus amyloliquefaciens* CJ14-6 strain selected from the strains with high protease activity isolated from traditional condiments can be used to prepare a soybean koji suitable for mass production of factory-made gochujang, thereby completing the present disclosure.

It is therefore an object of the present disclosure to provide a *Bacillus amyloliquefaciens* CJ14-6 strain isolated from traditional meju.

It is another object of the present disclosure to provide a method for preparing a soybean koji using the strain.

It is further another object of the present disclosure to provide a soybean koji prepared by the preparation method.

To achieve the objects of the present disclosure, there is provided a *Bacillus amyloliquefaciens* CJ14-6 strain isolated from traditional meju and having high protease activity and anti-obesity activity.

In accordance with the present disclosure, there is also provided a preparation method for soybean koji that includes a steaming step of soaking soybeans in water or adding waster to soybeans and steaming the soaked soybeans or the soybeans added water; and a making soybean koji step of inoculating a *Bacillus amyloliquefaciens* CJ14-6 strain into the steamed soybeans and fermenting the steamed soybeans.

In accordance with the present disclosure, there is also provided a soybean koji prepared by the preparation method.

Effects of the Invention

The present disclosure makes the effect to enable the production of factory-made gochujang in large quantities by using a *Bacillus amyloliquefaciens* CJ14-6 strain selected as a novel strain isolated from traditional meju and having high protease activity in the preparation of soybean koji.

BRIEF DESCRIPTIONS OF DRAWINGS

BEST MODES FOR CARRYING OUT THE INVENTION

Figure 1:
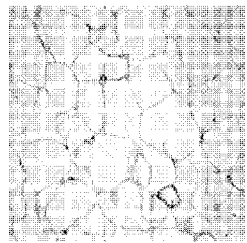
FIG. 1 is an image of adipocytes in the control group stained with anillin blue in Experimental Example 1.

Hereinafter, the present disclosure will be described in detail.

In accordance with a first embodiment of the present disclosure, there is provided a *Bacillus amyloliquefaciens* CJ14-6 strain isolated from traditional meju and having high protease activity.

More specifically, a variety of strains were isolated from Korean traditional meju. As a first selection out of the various strains, *Bacillus* spp. strains with high protease activity were isolated from the active medium; and as a second selection, from the *Bacillus* spp. strains, a strain with high proteolytic ability was separated from a solid culture medium using soybeans. 16s rDNA sequencing was adopted to identify the final selection of *Bacillus* spp. Strain.

The *Bacillus* spp. Strain isolated as the final selection was identified as *Bacillus amyloliquefaciens* (Sequence No. 1). This strain with high protease activity was named "*Bacillus amyloliquefaciens* CJ14-6" and accepted by the Korean Culture Center of Microorganisms (KCCM) on Jul. 1, 2015 (Accession No. KCCM11718P).

In accordance with a second embodiment of the present disclosure, there is provided a preparation method for soybean koji that includes a steaming step of soaking soybeans in water or adding waster to soybeans and steaming the soaked soybeans or the soybeans added water; and a making soybean koji step of inoculating a *Bacillus amyloliquefaciens* CJ14-6 strain into the steamed soybeans and fermenting the steamed soybeans.

More specifically, the present disclosure provides a preparation method for soybean koji that includes: soaking selected and washed soybeans in water or adding water to selected and washed soybeans; steaming and cooling down the soybeans; incubating a *Bacillus amyloliquefaciens* CJ14-6 strain to prepare a culture medium; and inoculating the culture medium, of the *Bacillus amyloliquefaciens* CJ14-6 strain into the cool soybeans and fermenting the soybeans to prepare a soybean koji.

The preparation method may further include a step of soaking the selected and washed soybeans in a soaking water maintained at 10 to 50° C. for 1 to 15 hours prior to the step of steaming soybeans. The soybeans may be steamed with saturated steam (1.0 to 2.0 kgf/cm$^2$) at 100 to 150° C. for 1 to 60 minutes. But, the steaming method available in the present disclosure is not limited to the specified method. The steamed soybeans may be cooled down to about 30 to 50° C., more specifically about 30 to 35° C.

The soybeans may be steamed in a high-pressure steam sterilizer (Autoclave) at 100 to 150° C. for 5 to 15 minutes, more specifically at 110° C. for 10 minutes.

The *Bacillus amyloliquefaciens* CJ14-6 strain may be used in the form of spores incubated in a culture medium. The culture medium, may be inoculated uniformly into the steamed soybeans in an amount of 0.1 to 3.0 wt. % with respect to the total weight of the soybean material.

The culture medium for incubation of the strain may be a soy sauce medium. The soy sauce medium as used herein may be prepared by mixing 1 to 10% of a soy sauce selected from the group consisting of a Korean-style soy sauce, a factory-made soy sauce, or a mixed soy sauce and 0.1 to 10% of a sugar selected from the group consisting of glucose, sucrose, galactose, and maltose.

In another embodiment of the present disclosure, the present disclosure includes inoculating a soy sauce medium (containing a factory-made soy sauce and glucose) with a *Bacillus amyloliquefaciens* CJ14-6 strain, acquired by pure culture isolation and stored, and conducting an incubation in the temperature range of 30 to 42° C. for 20 to 42 hours until the production of spores to prepare a culture medium for *Bacillus amyloliquefaciens* CJ14-6.

Following the inoculation of the *Bacillus amyloliquefaciens* CJ14-6, the soybeans are fermented at 30 to 45° C., more specifically at 34 to 44° C., for one to three days to prepare a soybean koji.

The preparation method may further include a drying step subsequent to the fermentation step.

In accordance with a third embodiment of the present disclosure, there is provided a soybean koji prepared by the preparation method for soybean koji.

The soybean koji prepared by the preparation method of the present disclosure may be used in the large-quantity production of factory-made gochujang.

Hereinafter, the present disclosure will be described in detail with reference to the following examples, which are given for the illustrations of the present disclosure only and not construed to limit the scope of the present disclosure.

EXAMPLES

Example 1: Isolation of Strain from Traditional Meju and Identification of Strain (1) Isolation of Strain and Identification The strain used as a fermentation starter in the present disclosure was isolated and selected from, traditional meju collected from the traditional food manufacturers in the Gyeonggi-do, Gangwon-do, Chungbuk, and Chunnam Provinces.

Traditional meju was diluted in sterilized water, spread, on a nutrient agar (Difco), and cultured at 37° C. Five microorganisms living as dominant species in the traditional meju were selected, isolated from, the traditional meju through the pure culture isolation method, and identified. The individual strains isolated were named 'CJ 3-27', 'CJ 4-4', 'CJ 5-10', 'CJ 14-6', and 'CJ 16-57', respectively.

The isolated strains were shaking-cultured (at 200 rpm) in a nutrient broth (Difco) at 37° C. for 24 hours and then measured in regards to protease activity. The results of identification and protease activity are presented in Table 1.

TABLE 1

Identification Result of Isolated Strains Derived from Traditional Meju

| Primary strain selections | Protease activity (U/g) | Identification results |
|---|---|---|
| CJ 3-27 | 62.58 ± 0.17 | *Bacillus amyloliquefaciens* |
| CJ 4-4 | 91.44 ± 6.97 | *Bacillus licheniformis* |
| CJ 5-10 | 61.72 ± 4.13 | *Bacillus subtilis* subsp. *Subtilis* |
| CJ 14-6 | 140.73 ± 4.62 | *Bacillus amyloliquefaciens* |
| CJ 16-57 | 222.42 ± 0.63 | *Bacillus licheniformis* |

(2) Primary Selection

The primary selections from the isolated and identified strains were the strains, such as CJ 3-27, CJ-4-4, CJ 14-6, and CJ 16-57, other than CJ 5-10 that has the lowest protease activity.

(3) Secondary Selection

The four strains given as the primary selections were used in the preparation of soybean koji and measured in regards to protease activity. The measurement results are presented in Table 2. Through a comparison of protease activity, strains with high protease activity were designated as a secondary selection.

For the preparation of soybean koji, 1 kg of soybeans were soaked in purified water for 12 hours, steamed in a high-pressure steam sterilizer (Autoclave) at 110° C. for 10 minutes, and then cooled down to 35° C. Each of the isolated strains was added to the cool soybeans in an amount of 2.0 wt. % with respect to the total weight of the material and incubated at 37° C. for 3 days. The strains thus cultured were used to prepare the individual soybean koji.

To measure the protease activity, each soybean koji was subjected to extraction and filtration at 30° C. for one hour, and the filtrate was used as a coenzyme solution. An enzyme reaction solution was prepared by adding 0.5 ml of the coenzyme solution, 1.5 ml of 2% milk casein as a substrate, and 1 ml of Mcllivine buffer (pH 6.0) and causing an enzyme reaction at 38° C. for one hour. Subsequently, 3 ml of 0.4 M TCA solution was added to suspend the reaction, and after a filtration, the reaction solution was sufficiently mixed with 5 ml of 0.4 M $Na_2CO_3$ and 1 ml of phenol reagent. The resultant solution was color-developed at 38° C. for 30 minutes, and the absorbance at 660 nm was determined with a spectrophotometer. In the expression of the enzyme activity, the amount of an enzyme producing tyrosine corresponding to 1 μg per minute was defined as one unit. Tyrosine was used as a reference substance to form a calibration curve.

TABLE 2

Comparison of Protease Activity for Soybean Koji Using Primary Strain Selections

| Primary strain selections | Protease activity (U/g) |
|---|---|
| CJ 3-27 | 258 |
| CJ 4-4 | 118 |
| CJ 14-6 | 225 |
| CJ 16-57 | 155 |

From the results of Table 2, CJ 3-27 and CJ 14-6 strains with high protease activity were selected.

(4) Third Selection: In-vitro 3T3-L1 Anti-obesity Activity
(A) Cell Line

As for fat differentiation cells, 3T3-L1 cells as a mouse embryonic fibroblast cell line were purchased from the Korean Cell Line Bank (KCLB).

(B) Cell Cultivation

The cultivation of 3T3-L1 cells was performed using a DMEM culture medium containing 10% BCS and 1% penicillin-streptomycin. The cells, when proliferated to 70% of the culture dish, were centrifugally separated at 1,000 rpm and sub-cultured at a ratio of 1:5.

(C) MTT Assay

Based on the ability of living cellular mitochondria dehydrogenase to react with MTT and form MTT formazan crystals in a dark blue color, the MTT assay was performed according to the method disclosed by Carmichael et al. 500 μl of 3T3-L1 cells per well were plated in a 48-well plate at a concentration of $1.5\times10^4$/ml and incubated in an incubator (37° C., 5% $CO_2$) for 24 hours so as to immobilize the cells on the bottom of the plate. In the next day, the sample was injected into each well to a final concentration of 1000 μg/ml, 250 μg/ml, or 0 μg/ml. After 24-hour incubation, the medium containing the sample was adjusted to 5 mg/ml and a thiazolyl blue tetrazolium bromide solution was added at a rate of 50 μl per well to a final concentration of 500 μg/ml. The cells were incubated in an incubator (37° C., 5% $CO_2$) for 4 hours. After the completion of the reaction, the medium, containing the MTT reagent was removed, and 300 μl of dimethyl sulfoxide (DMSO) was added to dissolve MTT-formazan crystals, which were color-developed for 5 minutes to measure the absorbance at 540 nm using an ELISA microplate reader.

(D) Induction of 3T3-L1 Cell Differentiation

In order to induce cell differentiation, the cells were plated in a 6-well plate at a concentration of $2.5\times10^4$/ml and incubated using a DMEM culture medium containing 10% FBS and 1% penicillin-streptomycin in an incubator (37° C., 5% $CO_2$) for 4 days until they got into the post-confluent state. The positive control used in the anti-obesity test was resveratrol capable of inhibiting the differentiation of pre-adipocytes, accelerating adipolysis, and preventing adipogenesis by inducing the self-directed cellular 'suicide' of mature adipocytes.

On the $0^{th}$ day, the cells in the post-confluent, state were treated with a differentiation-inducing medium containing 10% FBS, 1% penicillin-streptomycin, 5 μg/ml insulin, 1 μM dexamethasone (DMS), and 0.5 mM (3-isobutyl-1-methylxanthine (IBMX) for 72 hours. On the $3^{rd}$ and $5^{th}$ days, the cells were incubated with a DMEM differentiation-activating culture medium containing 10% FBS, 1% penicillin-streptomycin, and 10 μg/ml INS. Whenever the medium was replaced, all the samples were treated to have a concentration of 10 μg/ml, 50 μg/ml, or 0 μg/ml and adjusted to a concentration of 20 μg/ml as a positive control.

(E) Oil Red Q Dyeing and Quantification

In order to determine the degree of differentiation of 3T3-L1 cells during incubation, the cells were, stained with an Oil Red O reagent for dyeing lipid droplets according to a modification of the method disclosed by Rene et al., and Kasturi et al. on the $7^{th}$ day, that is, the last day of differentiation.

The cells under differentiation were immobilized in each well containing 4% para-formaldehyde (in PBS) through a reaction at room temperature for one hour or longer. The cells were removed of the immobilization solution and stained with 0.5% Oil Red 0 for one hour. For removal of the remaining dye, the cells were washed with flowing water twice until none of the dyeing reagent left. The stained lipid droplets were dissolved in isopropanol and measured in regards to the absorbance at 510 nm.

The in-vitro anti-obesity activity was determined by comparison of the adipocyte differentiation inhibitory activity between the two stains of Bacillus amyloliquefaciens, CJ 3-27 and CJ 14-6, which proved to have high protease activity.

TABLE 3

Adipocyte differentiation inhibition rate of secondary strain selections

| Strains | Concentration of culture medium (μg/ml) | Differentiation inhibition rate (%) |
|---|---|---|
| Bacillus amyloliquefaciens CJ 3-27 | 25 | 10.10 |
|  | 50 | 6.98 |
|  | 100 | 3.37 |
| Bacillus amyloliquefaciens CJ 14-6 | 25 | 20.57* |
|  | 50 | 26.41* |
|  | 100 | 36.61* |

Statistic calibration: student-T test
*P < 0.05

As can be seen from the results of Table 3, the CJ 14-6 strain culture medium showed a significant level of adipocyte differentiation inhibition rate, while the CJ 3-27 strain culture medium, had no significant change in the adipocyte differentiation inhibition rate.

Example 2: Preparation of Soybean Koji

The final selection of novel strain in. Example, *Bacillus amyloliquefaciens* CJ 14-6, was used as a fermentation starter to prepare a soybean koji according to the preparation method as stated in Example 1-(1).

For a comparison with a conventional soybean koji using *Aspergillus oryzae*, a soybean koji was prepared using *Aspergillus oryzae* commercially available from Chungmoo Fermentation Co. as a fermentation starter according to the preparation method as stated in Example 1-(1).

(1) Measurement of Protease Activity

Each soybean koji was measured in regards to protease activity. The measurement results are presented in Table 4.

TABLE 4

: Enzyme activity of soybean koji using novel *Bacillus amyloliquefaciens* CJ 14-6 strain and conventional *Aspergillus oryzae* strain

| Strains | Protease activity (U/g) |
|---|---|
| Novel *Bacillus amyloliquefaciens* CJ 14-6 | 225 |
| Conventional *Aspergillus oryzae* | 102 |

As can be seen from the results of Table 4, the soybean koji using the novel *Bacillus amyloliquefaciens* CJ 14-6 strain was 120.6% higher in the protease activity than the soybean koji using the convention *Aspergillus oryzae* strain. This shows that the use of the soybean koji using the novel *Bacillus amyloliquefaciens* CJ 14-6 strain can promote the protein degradation activity when used in gocnujang or doenjang and contribute to the enhancement of the taste qualities.

Experimental Example 1: Measurement of Anti-Obesity Effect of Soybean Koji Using Novel Strain (CJ 14-6)

An animal experiment was conducted in order to evaluate the anti-obesity effect of the soybean koji using the novel *Bacillus amyloliquefaciens* CJ 14-6 strain. The animals used in the experiment were male white rats (S.D. rat, 5 weeks old), which were purchased from Damool Science (South Korea) and kept in vivariums maintained at 18±2° C. under illumination regulated on a cycle of 12 hours (from 08:00 to 20:00).

Rat objects were divided into two groups, each group consisting of seven objects. In the control group, 20% of lard was added to the powdery feed for white rat, and the rat objects were fed on a high-fat diet. In the Example-2 group, the rat objects were fed with 0.91% of the soybean koji using the novel strain of the present disclosure on the same high-fat diet. The weight and the adipose-tissue weight of the rat objects are presented in Tables 5 and 6, respectively.

The weight and the diet intake were measured every week, and the adipose-tissue weight and the lipid content were determined after a 12-hour fasting prior to the termination of the testing. The collected blood was centrifugally separated at 1,900×G for 20 minutes to isolate the blood serum, which was used as a sample for determination of the lipid content in blood serum. In order to analyze the total lipid content, the neutral fat content, and the total cholesterol content, of liver and adipose tissues, chloroform-methanol (2:1, v/v) was added to 0.1 g of the collected liver and adipose tissues, which were then kept refrigerated for 3 days and soaked in distilled water. The liver and adipose tissues were centrifugally separated at 1,150×G for 20 minutes and measured in regards to the total lipid content in the lipid layer, that is, the bottom, layer. The lipid tissue was diluted and used to determine the total cholesterol content and the neutral fat content. The lipid content in the blood serum and tissues through the content analyses are presented in Tables 7 to 10.

In order to measure the enzyme activity related to the biosynthesis of fatty acid in the adipose tissue, a 0.1 M potassium phosphate buffer (pH 7.4, 37° C.) in a volume three times as much as the weight of the adipose tissue was added, and after homogenization, the adipose tissue was centrifugally separated at 3,000 rpm for 15 minutes. The supernatant thus obtained was centrifugally separated at 15,000 rpm for 30 minutes to collect a second supernatant. The enzyme activity measurements are presented in Tables 11 and 12.

To determine the size of the adipocytes, the adipocytes collected were immobilized with a Bouin solution to make a paraffin block, which was cut into slices and stained with an anillin blue dye. Subsequently, the images of the adipocytes were taken with an electronic microscope to compare the adipocytes in each treated region.

TABLE 5

| Groups | Initial body weight (g) | Final body weight (g) | Body weight increment (g/day) | Daily diet intake (g/day) |
|---|---|---|---|---|
| Control group | 171.79 | 544.00 | 6.84 ± 0.40 | 17.49 ± 0.80 |
| Example-2 group | 172.57 | 513.29 | 6.26 ± 0.40 | 17.33 ± 1.78 |

TABLE 6

| | Adipose tissue weight (g/100 g body wt.) | | |
|---|---|---|---|
| Groups | Fat in epididymis | Fat around kidney | Total white fat |
| Control group | 2.43 | 0.78 | 6.80 |
| Example-2 group | 2.24 | 0.65 | 6.29 |

TABLE 7

| | Lipid content in blood serum (mg/dl) | | |
|---|---|---|---|
| Groups | Neutral fat | Total cholesterol | LDL-cholesterol |
| Control group | 225.57 ± 25.64 | 128.43 ± 12.92 | 125.40 ± 15.43 |
| Example-2 group | 152.57 ± 10.21*** | 95.86 ± 8.28*** | 63.66 ± 8.75*** |

TABLE 8

| | Lipid content in liver tissue (mg/g) | | |
|---|---|---|---|
| Groups | Total fat | Neutral fat | Total cholesterol |
| Control group | 247.02 ± 21.87 | 94.91 ± 18.43 | 360.45 ± 57.55 |
| Example-2 group | 220.99 ± 16.77* | 64.57 ± 3.00** | 292.48 ± 76.68 |

TABLE 9

Lipid content in epididymis adipose tissue (mg/g)

| Groups | Total fat | Neutral fat | Total cholesterol |
|---|---|---|---|
| Control group | 501.55 ± 57.14 | 166.15 ± 16.18 | 294.90 ± 15.00 |
| Example-2 group | 459.50 ± 35.17 | 118.44 ± 18.44*** | 250.48 ± 26.74** |

TABLE 10

Lipid content in mesenteric adipose tissue (mg/g)

| Groups | Total fat | Neutral fat | Total cholesterol |
|---|---|---|---|
| Control group | 412.22 ± 37.59 | 122.01 ± 6.02 | 178.23 ± 24.41 |
| Example-2 group | 368.37 ± 23.66* | 108.81 ± 9.02** | 147.77 ± 12.72* |

TABLE 11

Enzyme related to fatty acid synthesis in liver tissue (nmol/min/mg protein)

| Groups | FAS | ME | G6PDH |
|---|---|---|---|
| Control group | 12.22 ± 1.07 | 31.47 ± 1.39 | 24.68 ± 1.45 |
| Example-2 group | 9.77 ± 0.54 | 26.96 ± 1.74 | 17.31 ± 1.19** |

TABLE 12

Enzyme related to fatty acid synthesis in adipose tissue (nmol/min/mg protein)

| Groups | FAS | ME | G6PDH |
|---|---|---|---|
| Control group | 7.29 ± 0.59 | 8.00 ± 0.31 | 24.62 ± 1.26 |
| Example-2 group | 5.35 ± 0.35* | 5.51 ± 0.62** | 20.21 ± 1.30* |

TABLE 13

Figure 2:
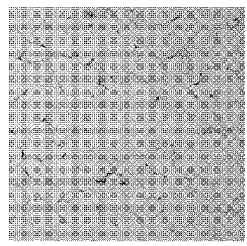
FIG. 2 is an image of adipocytes in the Example-2 test group stained with anillin blue in Experimental Example 2.

| | Groups | |
|---|---|---|
| | Control group | Example-2 group |
| Image of adipocyte | Refer to FIG. 1 | Refer to FIG. 2 |
| Size of adipocyte ($\mu m^2$) | 21.41 ± 2.45 | 18.18 ± 1.11 |

TABLE 14

| | Body fat accumulation index factors | | |
|---|---|---|---|
| Groups | Leptin (µg/ml) | HR-LPL (unit/g) | TE-LPL (unit/g) |
| Control group | 5.75 ± 0.70 | 7.03 ± 1.08 | 36.12 ± 5.50 |
| Example-2 group | 3.97 ± 0.17*** | 4.30 ± 1.06** | 22.74 ± 2.08*** |

Statistic calibration: student-T test
*$P < 0.05$
**$P < 0.01$
***$P < 0.001$

As can be seen from the results of Table 5, the Example-2 group had a body weight increment accounting for no more than 91.5% of the body weight increment of the control group. According to the results of Table 6, the Example-2 group was lower in the weight of the adipose tissue around the kidney than the control group; so the weight of the adipose tissue around the kidney in the Example-2 group accounted for no more than 83.3% of that in the control group.

Accordingly, the results of the example show that the soybean koji using a novel strain (CJ 14-6) makes an effect to reduce the body weight.

[Accession Number]

Depository Institution: Korean Culture Center of Microorganisms (Abroad)

Accession No.: KCCM11718P

Date of Deposit: Jul. 1, 2015

The invention claimed is:

1. A method for preparing a soybean koji, comprising:
soaking soybeans in water or adding water to soybeans, and steaming the soybeans;
inoculating a *Bacillus amyloliquefaciens* CJ 14-6 strain, deposited in the Korean Culture Center of Microorganisms under Accession number KCCM 11718, into the steamed soybeans; and
fermenting the steamed soybeans to prepare a soybean koji having degraded protein.

2. The method as claimed in claim 1,
wherein the method further includes soaking selected and washed soybeans at 10 to 50° C. for 1 to 15 hours prior to the steaming step,
wherein the steaming step includes forcing a saturated steam of 1.0 to 2.0 kgf/cm2 to steam the soybeans at 100 to 150° C. for 1 to 60 minutes, and
wherein the method further includes cooling down the steamed soybeans to 30 to 50° C. after the steaming step.

3. The method as claimed in claim 1, wherein the steaming step is conducted in a high-pressure steam sterilizer (Autoclave) at 100 to 150° C. for 5 to 15 minutes.

4. The method as claimed in any one of claim 1, wherein the *Bacillus amyloliquefaciens* CJ 14-6 strain is inoculated into the steamed soybeans in an amount of 0.1 to 3.0 wt. % with respect to the total weight of raw materials.

* * * * *